United States Patent
Tamasikné Helyes et al.

(10) Patent No.: US 9,790,193 B2
(45) Date of Patent: Oct. 17, 2017

(54) SEMICARBAZIDE-SENSITIVE AMINE OXIDASE INHIBITORS FOR USE AS ANALGESICS IN TRAUMATIC NEUROPATHY AND NEUROGENIC INFLAMMATION

(71) Applicant: PÉCSI TUDOMÁNYEGYETEM, Pécs (HU)

(72) Inventors: Zsuzsanna Tamasikné Helyes, Pécs (HU); Valéria Dezsö-Tékus, Pécs (HU); Bálint Scheich, Pécs (HU); Péter Mátyus, Budapest (HU)

(73) Assignee: PÉCSI TUDOMÁNYEGYETEM, Pécs (HU)

(*) Notice: Subject to any disclaimer, the term of this patent is extended or adjusted under 35 U.S.C. 154(b) by 0 days.

(21) Appl. No.: 15/303,794

(22) PCT Filed: Dec. 18, 2014

(86) PCT No.: PCT/HU2014/000127
§ 371 (c)(1),
(2) Date: Oct. 13, 2016

(87) PCT Pub. No.: WO2015/159112
PCT Pub. Date: Oct. 22, 2015

(65) Prior Publication Data
US 2017/0044117 A1    Feb. 16, 2017

(30) Foreign Application Priority Data
Apr. 15, 2014 (HU) .............................. 1400205
Oct. 8, 2014 (HU) .............................. 1400479

(51) Int. Cl.
C07D 263/32 (2006.01)
A61K 31/15 (2006.01)
(Continued)

(52) U.S. Cl.
CPC ............ *C07D 263/32* (2013.01); *A61K 31/15* (2013.01); *A61K 31/404* (2013.01);
(Continued)

(58) Field of Classification Search
None
See application file for complete search history.

(56) References Cited

U.S. PATENT DOCUMENTS 8,536,210 B2    9/2013  Matyus et al.
2005/0096360 A1    5/2005  Salter-Cid et al.
(Continued)

FOREIGN PATENT DOCUMENTS

WO    96/31460 A1    10/1996
WO    2006094201    *    9/2006
WO    2010029379    *    3/2010

OTHER PUBLICATIONS

Salter-Cid et al., Journal of Pharmacology and Experimental Therapeutics (2005), 315(2), 553-562.*
(Continued)

*Primary Examiner* — Karl J Puttlitz
(74) *Attorney, Agent, or Firm* — Jason D. Voight

(57) ABSTRACT

The invention relates to a compound having SSAO/VAP-1 inhibitor activity for use in the treatment of hyperalgesia and allodynia implicated in traumatic neuropathy or neurogenic inflammation. Accordingly, the invention relates to a compound having SSAO/VAP-1 inhibitor activity for use in the inhibition of pathological activation and dysfunctions of peptidergic sensory nerves caused by mechanical damage or chemical activation of peptidergic sensory nerves in neurogenic inflammation.

7 Claims, 10 Drawing Sheets

(51) Int. Cl.
*A61K 31/404* (2006.01)
*A61K 31/417* (2006.01)
*A61K 31/50* (2006.01)
*A61K 31/513* (2006.01)
*C07C 243/18* (2006.01)

(52) U.S. Cl.
CPC ............ *A61K 31/417* (2013.01); *A61K 31/50* (2013.01); *A61K 31/513* (2013.01); *C07C 243/18* (2013.01)

(56) References Cited

U.S. PATENT DOCUMENTS

2007/0066646 A1 3/2007 Clauzel et al.
2008/0269282 A1 10/2008 Clauzel et al.

OTHER PUBLICATIONS

Wang et al., Journal of Medicinal Chemistry, 2006, vol. 49, No. 7.*
Baron: "Neuropathic Pain: A Clinical Perspective", Handbook of Experimental Pharmacology, 2009, vol. 194, pp. 3-30.
Botz et al.: "Challenges to develop novel anti-inflammatory and analgesic drugs", WIREs Nanomed Nanobiotechnol, 2016, doi: 10.1002/anan.1427.
Littlejohn: "Neurogenic neuroinflammation in fibromyalgia and complex regional pain syndrome", Nat. Rev. Rheumatol., 2015, doi:10.1038/nrrheum.2015.100, pp. 1-10.
Berger et al.: "Cellular and molecular insights into neuropathy-induced pain hypersensitivity for mechanism-based treatment approaches", Brain Research Reviews, 2011, vol. 67, pp. 282-310.
Finnerup et al.: "The evidence for pharmacological treatment of neuropathic pain", International Association for the Study of Pain, 2010, vol. 150, pp. 573-581.
Kerstman et al.: "Neuropathic pain", Handbook of Clinical Neurology, 2013, vol. 110, pp. 175-187.
Truini et al.: "Reappearing neuropathic pain in humans—how symptoms help disclose mechanisms", Nat. Rev. Neurol., 2013, doi:10.1038/nrneurol.2103.180; pp. 1-11.
Vranken: "Mechanisms and Treatment of Neuropathic Pain", Central Nervous Systems Agents in Medicinal Chemistry, 2009, vol. 9, pp. 71-78.
Atzeni et al.: "Pain in systemic inflammatory rheumatic diseases", Best Practice & Research Clinical Rheumatology, 2015, pp. 1-11.
Jensen et al.: "Allodynia and hyperalgesia in neuropathic pain: clinical manifestations and mechanisms", Lancet Neurol, 2014, vol. 13, pp. 924-935.
Marchettini et al.: "Painful Peripheral Neuropathies", Current Neuropharmacology, 2006, vol. 4, pp. 175-181.

* cited by examiner

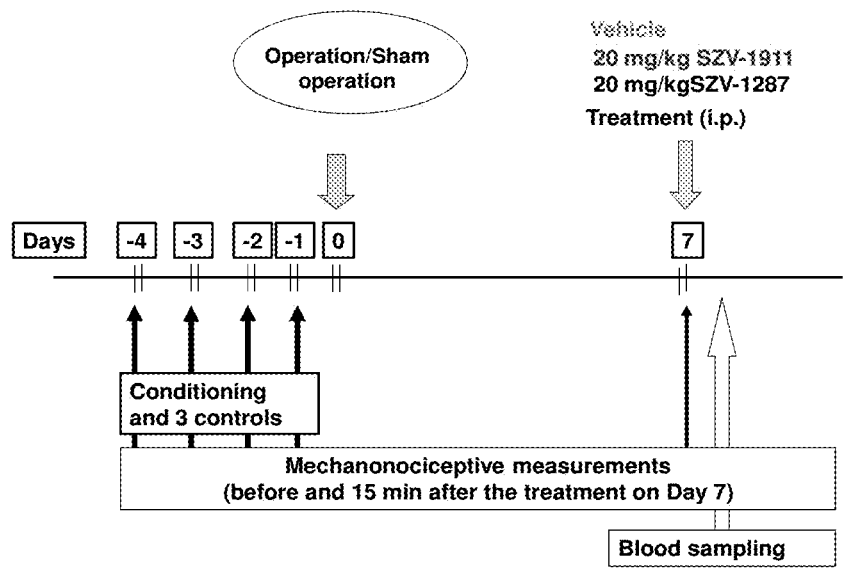
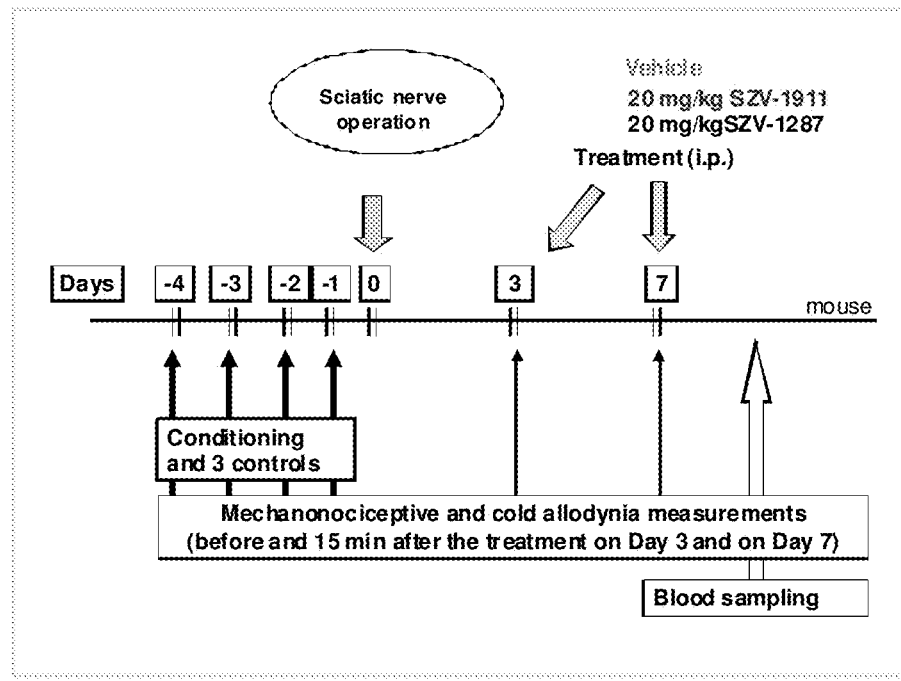
Figures 1 A and B

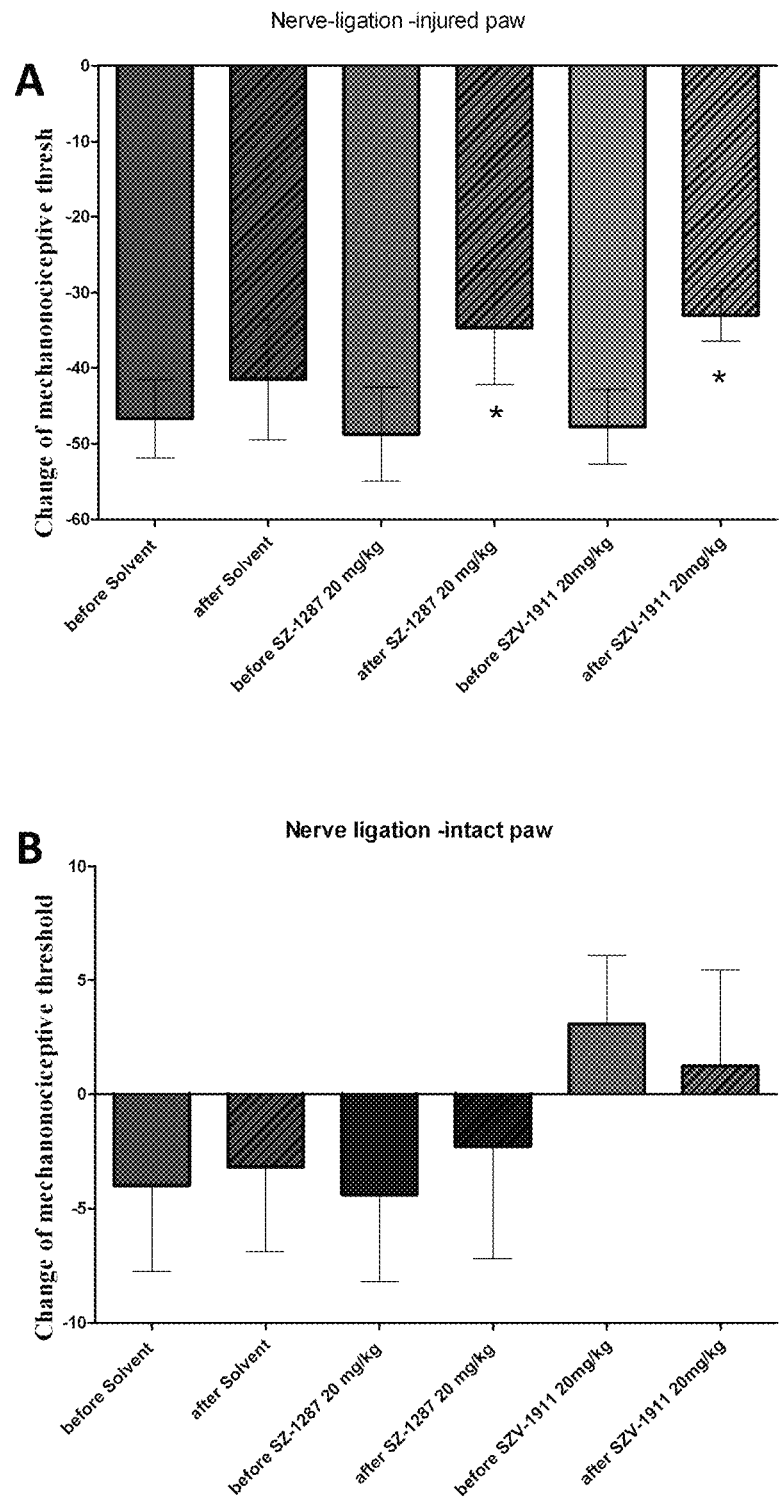
*Figures 2 A and B*

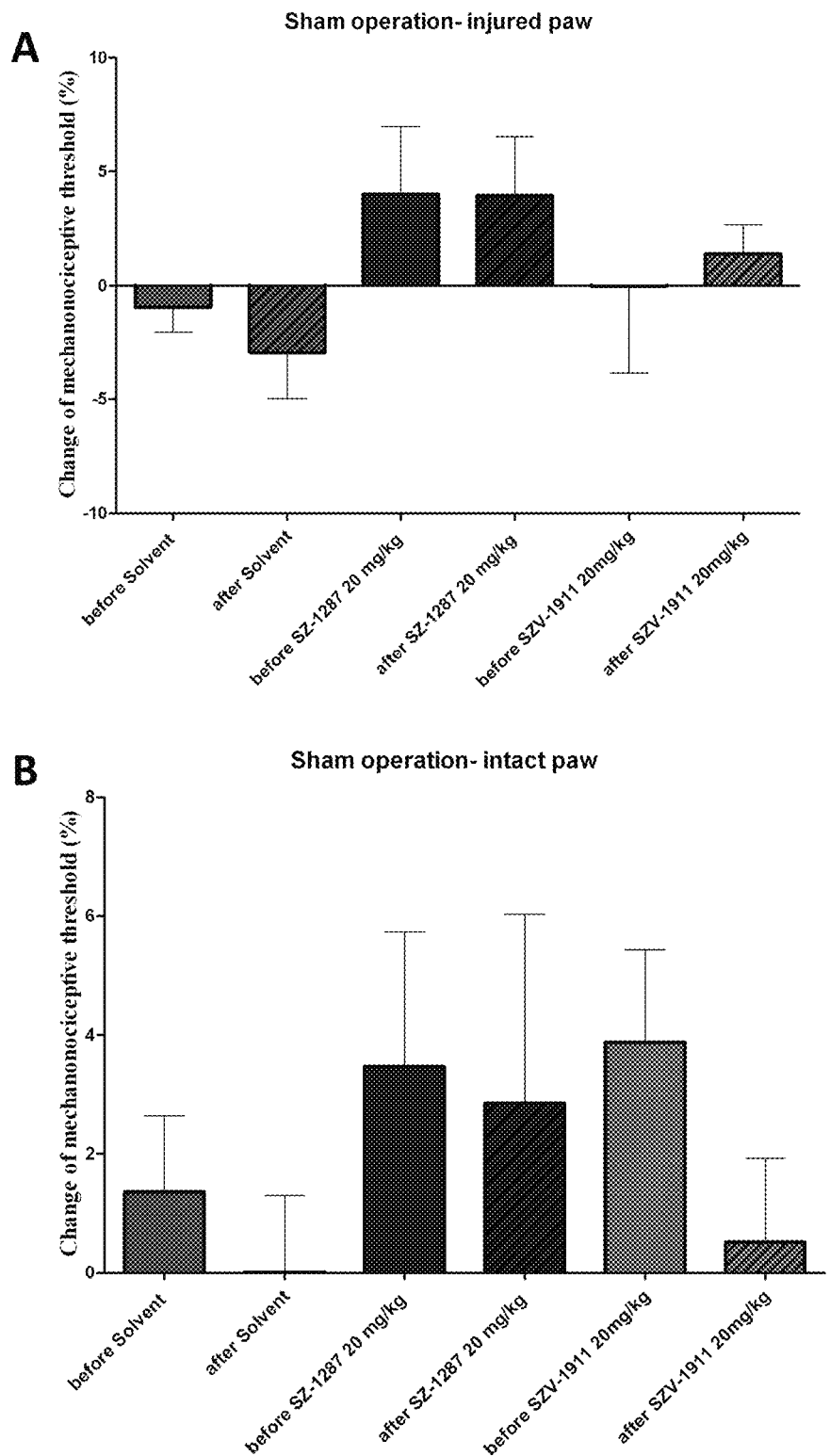
*Figures 3 A and B*

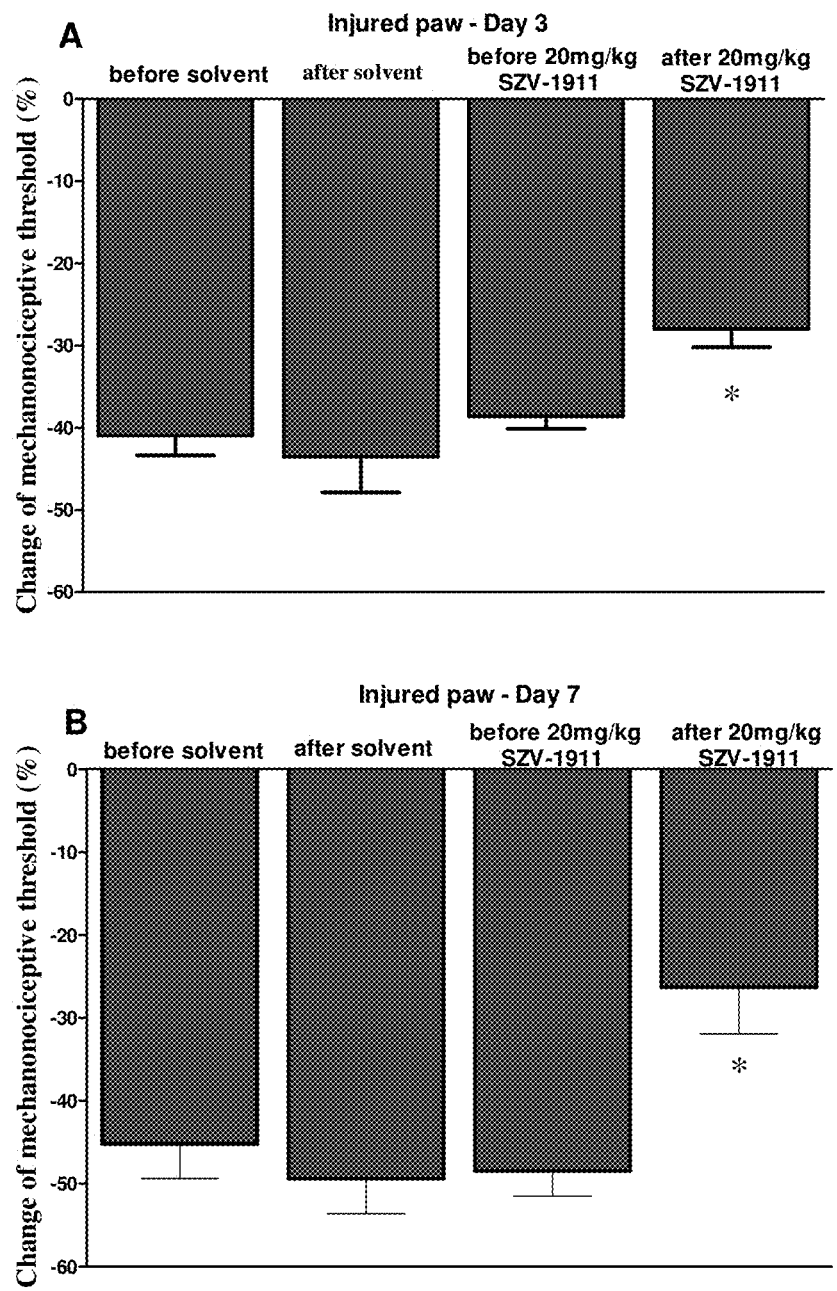
*Figures 4 A and B*

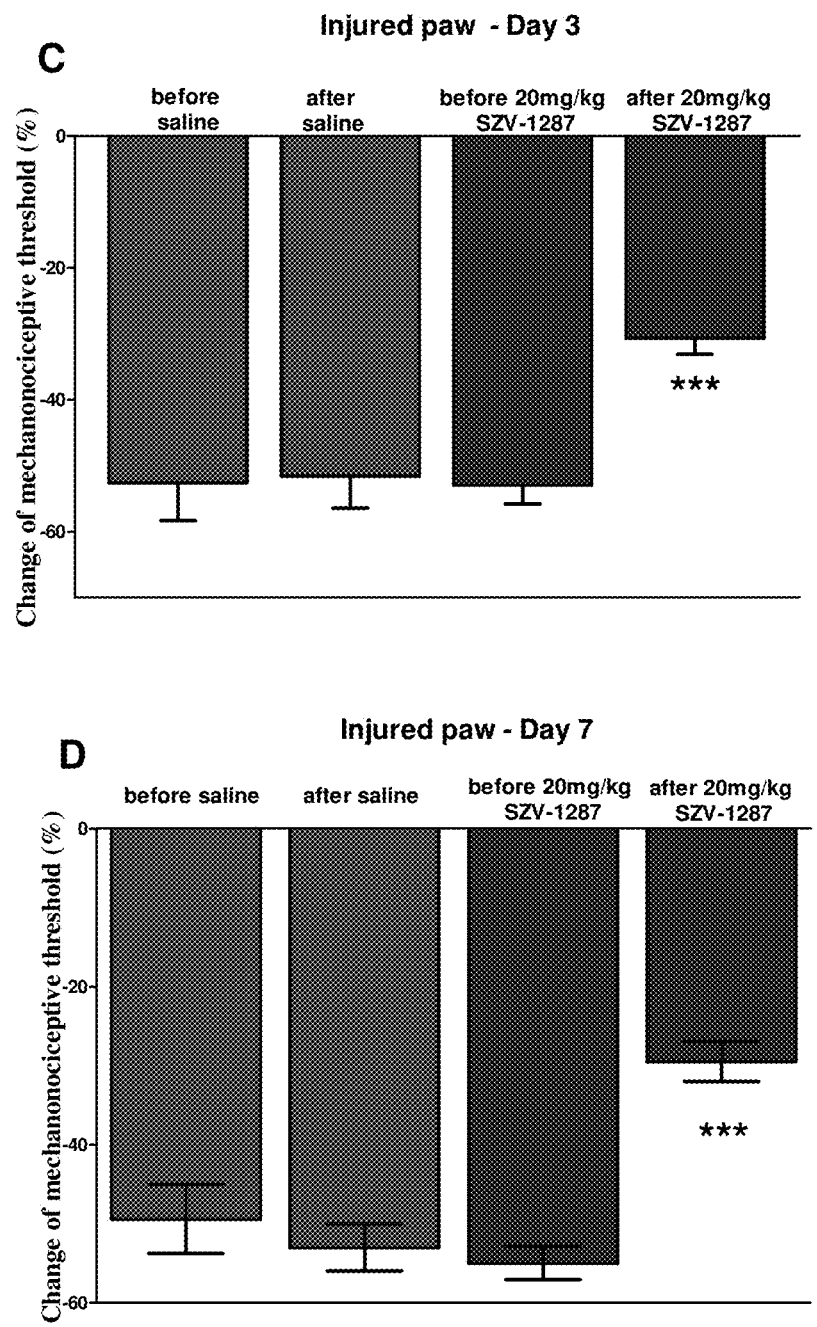
Figures 4 C and D

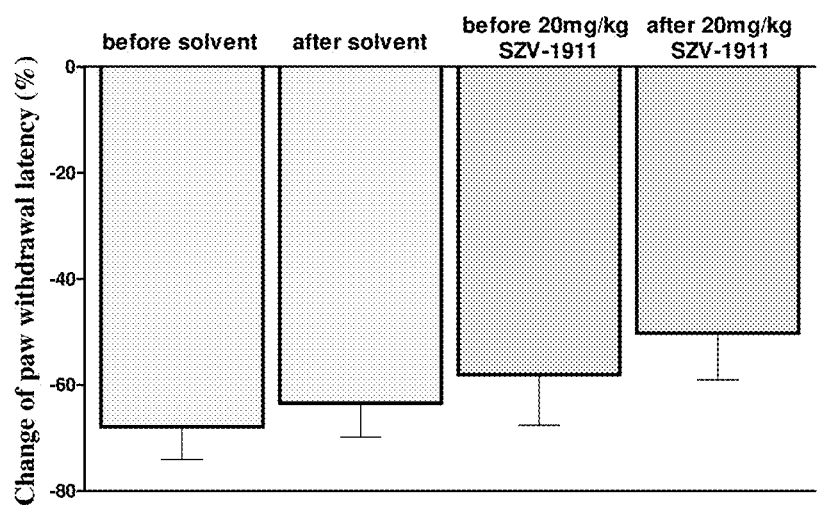
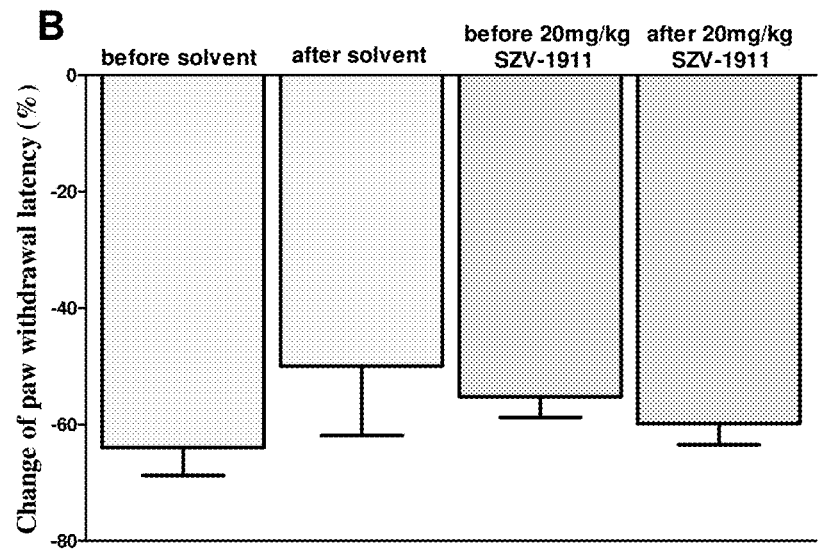
*Figures 5 A and B*

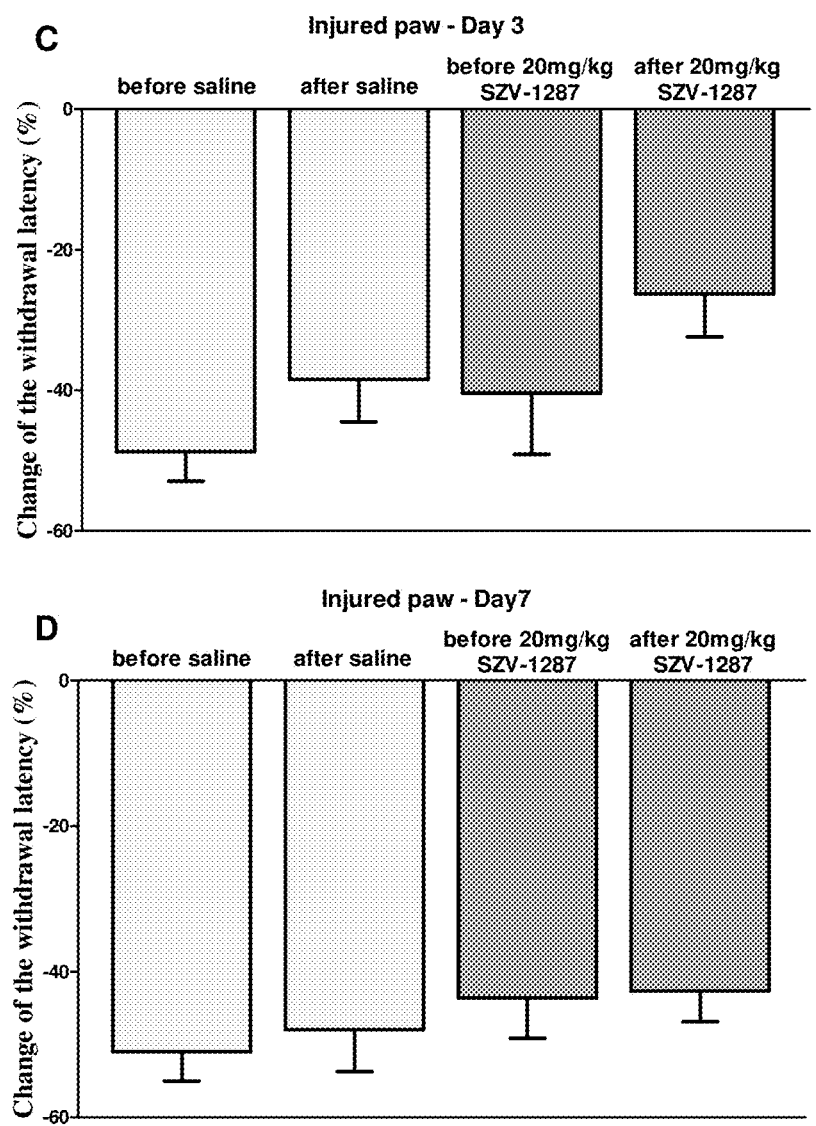
*Figures 5 C and D*

A
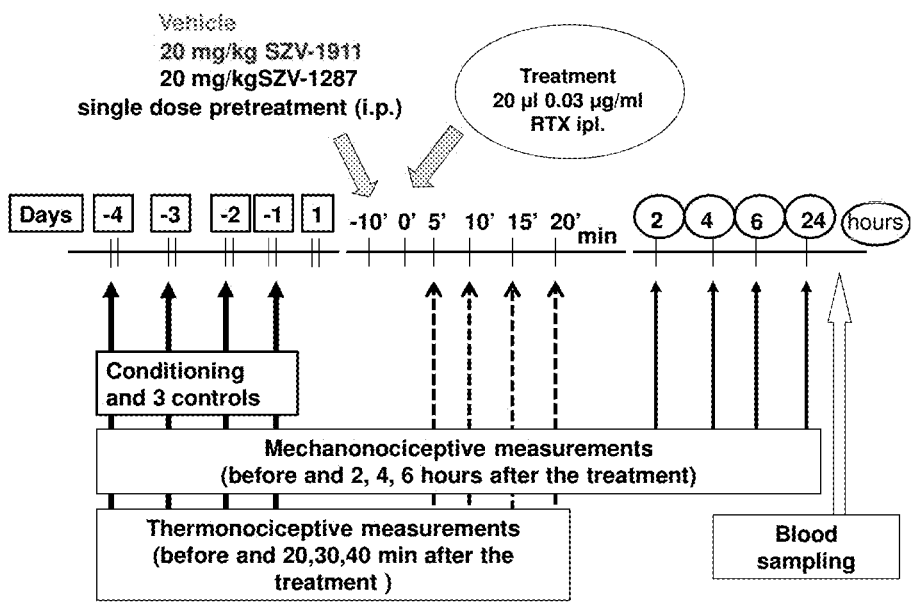
B
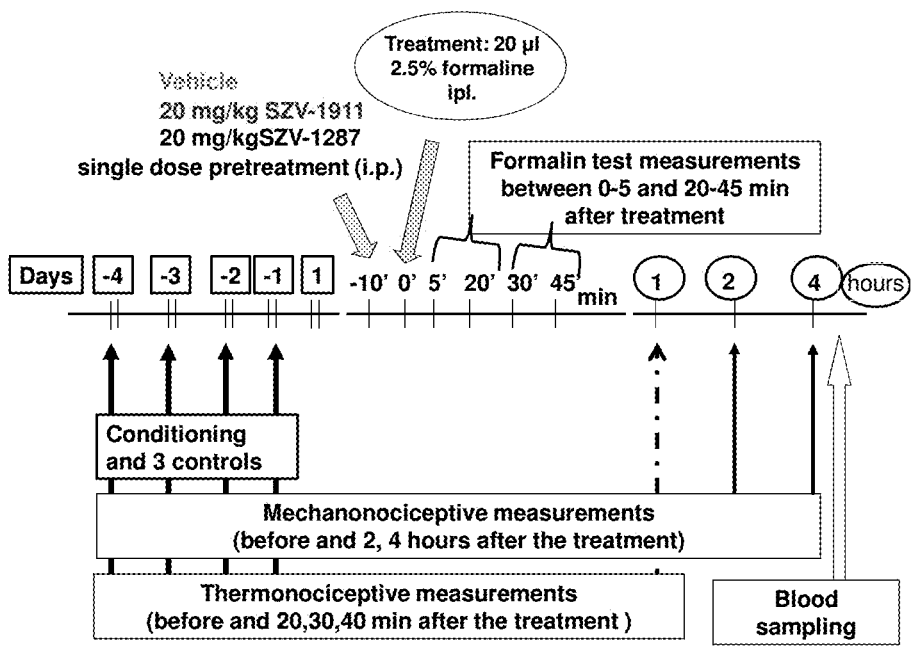
*Figures 6 A and B*

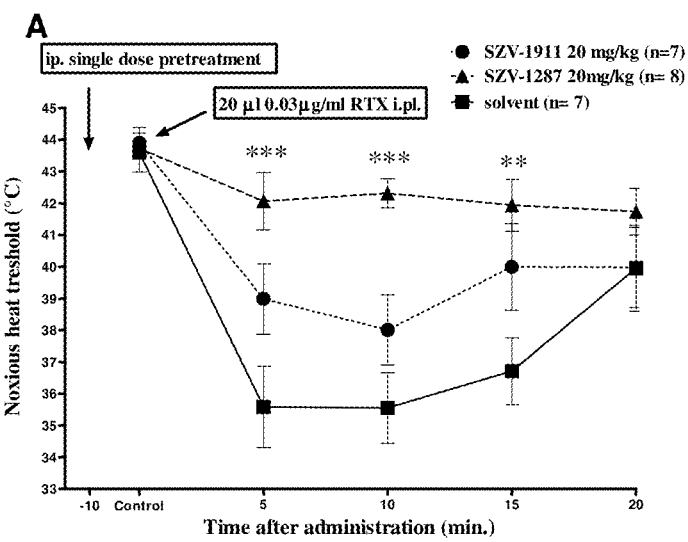
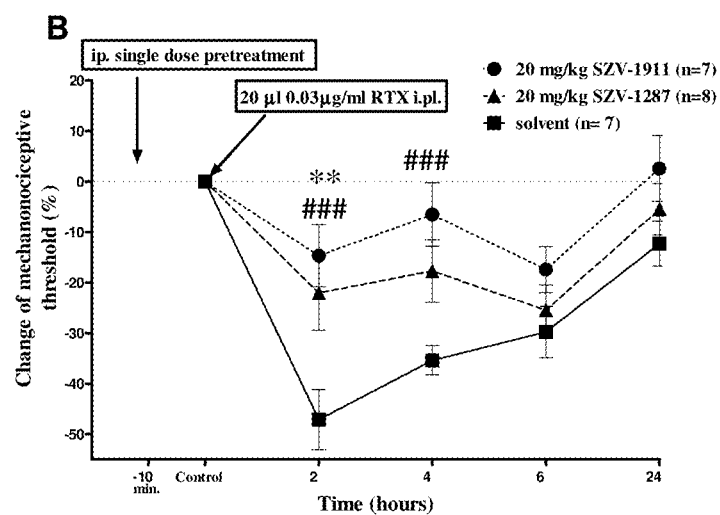
Figures 7 A and B

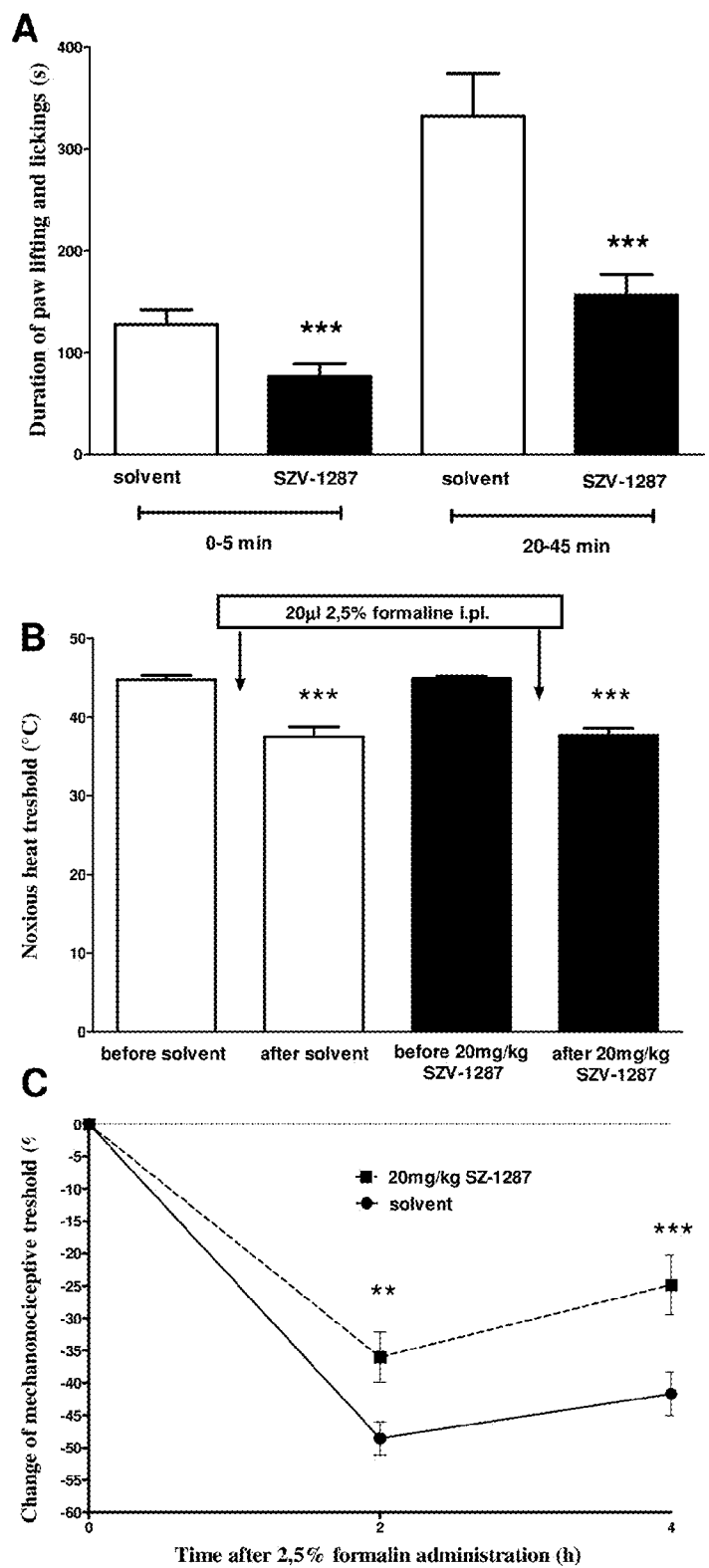
*Figures 8 A, B and C*

SEMICARBAZIDE-SENSITIVE AMINE OXIDASE INHIBITORS FOR USE AS ANALGESICS IN TRAUMATIC NEUROPATHY AND NEUROGENIC INFLAMMATION

This is the national stage of International Application PCT/HU2014/000127, filed Dec. 18, 2014.

TECHNICAL FILED OF THE INVENTION

The present invention is based on potent analgesic (antihyperalgesic) effect of semicarbazide-sensitive amine oxidase (SSAO) also known as vascular adhesion protein 1 (VAP-1) inhibitors.

This novel indication has not yet been suggested by previous data and cannot be extrapolated either from earlier published roles of this enzyme, such as its well-established function in inflammation and metabolic disorders, or the described actions of the specific enzyme inhibitors.

BACKGROUND OF THE INVENTION

Semicarbazide sensitive amine oxidase (SSAO)/vascular adhesion protein-1 (VAP-1) is a membrane protein with a dual function. On the one hand, SSAO [EC 1.4.3.6] belongs to the family of copper-containing amine oxidases, its name deriving from its sensitivity to inhibition by a type of carbonyl reagents called semicarbazide (Lyles G A, Int. J. Biochem. Cell. Biol., 1996, 28, 259-274). SSAO catalyzes the oxidative deamination of primary aliphatic and aromatic amines with the following reaction pathway.

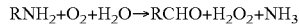

$RNH_2 + O_2 + H_2O \rightarrow RCHO + H_2O_2 + NH_3$

The enzymatic reaction of the amine results in the formation of the corresponding aldehyde, $H_2O_2$ and ammonia; the products formed in the reaction being generally more cytotoxic than the substrates themselves. For the human enzyme, aminoacetone and methylamine have been identified as endogenous physiological substrates.

On the other hand, analyis of the genetic encoding of an adhesion protein revealed the identity of SSAO and human vascular adhesion protein-1 (VAP-1) (Smith D J et al., J. Exp. Med., 1998, 188, 17-27). VAP-1 is a cell adhesion molecule with some special features distinguishing it from other adhesion molecules related to inflammation, such as the monoamine oxidase activity and a restricted expression pattern (Salmi M et al., Science, 1992, 257, 1407-1409; Smith D J et al., J. Exp. Med., 1998, 188, 17-27). The level of VAP-1 is upregulated in the vasculature at sites of inflammation.

Although the substrate specificity of SSAO/VAP-1 partly overlaps with that of monoamine oxidases (MAOs), SSAO/VAP-1 differs from MAO A and MAO B with respect to cofactor (2,4,5-trihydroxy-phenylalanyl quinone (TPQ) for SSAO/VAP-1), biological function, substrates (there are some distinctive substrates), inhibitors and subcellular distribution. Products of SSAO/VAP-1, such as formaldehyde are mainly extracellular. The absence of formaldehyde dehydrogenase from the blood plasma, where SSAO/VAP-1 products are formed, may amplify the potential toxic effects of formaldehyde towards blood vessels.

SSAO/VAP-1 exists as a membrane-bound and as a soluble form in the plasma, its activity displaying a wide tissue distribution. It has been hypothesized that the soluble form is generated via proteolytic cleavage from the membrane-bound form. The major sources of the enzyme are the endothelial cells, smooth muscle cells and adipocytes. Because expression of SSAO is particularly remarkable in the endothelium and the plasma, cytotoxic effects associated with the enzyme may be increased in the highly vascularised tissues, such as the eyes and kidneys, partially explaining late-diabetic complications (Ekblom J. et al., Pharmacol. Res., 1998, 37, 87-92).

SSAO/VAP-1 has a role in the metabolism of biogenic and xenobiotic amines. Products formed in the enzyme reaction (formaldehyde, methylglyoxal and $H_2O_2$ for the endogenous substrates) may be involved in processes such as protein cross-linking, formation of advanced-glycation end products or increase of oxidative stress. Higher concentrations of the physiological substrates in diabetes together with the higher enzyme activity observed may lead to a higher production of the cytotoxic agents, therefore may lead to diabetes-associated complications. Treatment of diabetes-associated vasculopathies such as retinopathy, neuropathy and nephropathy with enzyme inhibitors has been proposed.

SSAO/VAP-1 expression is induced during adipogenesis (Fontana E et al., Biochem. J., 2001, 356, 769-777; Moldes M et al., J. Biol. Chem., 1999, 274, 9515-9523), therefore a role for SSAO/VAP-1 in the adipogenic gene program has been suggested. Due to its special features in adipose tissue, SSAO/VAP-1 has been proposed as a potential target for the treatment of obesity (Bour S et al., Biochimie, 2007, 89, 916-925).

SSAO/VAP-1 as an adhesion molecule plays a role in leukocyte trafficking and is involved in an adhesive cascade leading to the transmigration of leukocytes into inflamed tissues from the circulation. In the adhesion cascade both the amine oxidase and the adhesive function of SSAO/VAP-1 take part (Salmi M et al., Immunity, 2001, 14, 265-276), a direct interaction with a leukocyte surface substrate mediating the leukocyte-SSAO/VAP-1 interaction has been proposed. Products of the enzyme reaction of SSAO/VAP-1, such as $H_2O_2$, a signalling molecule itself, via the upregulation of other adhesion molecules leading to enhanced leukocyte trafficking may contribute to the escalation of the inflammatory process. Therefore, inhibitors of the enzymatic activity may serve as useful antiinflammatory agents.

SSAO/VAP-1 inhibitors could reduce leukocyte trafficking at sites of inflammation and therefore reduce the inflammatory process as proved by several animal studies (for example: ulcerative colitis—Salter-Cid L M et al., J. Pharm. Exp. Ther., 2005, 315, 553-562; arthritis—Marttila-Ichihara F et al., Arthritis Rheum., 2006, 54, 2852-282862; multiple sclerosis—Wang E Y et al., J. Med. Chem., 2006, 49, 2166-2173; uveitis—Noda K et al., FASEB J., 2008, 22, 1094-1103). As translocation of VAP-1 to the endothelial cell surface occurs at sites of inflammation, modulation of the normal immune system could be avoided by the use of SSAO/VAP-1 as a novel anti-inflammatory target.

In healthy humans, the plasma SSAO/VAP-1 activity is rather constant. Elevated SSAO/VAP-1 levels or overexpression of the enzyme have been observed in various pathological conditions or diseases, such as diabetes (both type I and type II), particularly in the presence of diabetic complications (Boomsma F et al., Biochim. Biophys. Acta, 2003, 1647, 48-54; Boomsma F, Clin. Sci., 1995, 88, 675-679; Garpenstrand H et al., Diabetic. Med., 1999, 16, 514-521; Meszaros Z et al., Metab. Clin. Exp., 1999, 48, 113-117; Boomsma F et al., Diabetologia, 1999, 42, 233-237; Salmi M et al., Am. J. Pathol., 2002, 161, 2255-2262), congestive heart failure (Boomsma F et al., Cardiovasc. Res., 1997, 33, 387-391), obesity (Meszaros Z et al., Metab.

Clin. Exp., 1999, 48, 113-117; Weiss H G et al., Metab. Clin. Exp., 2003, 52, 688-692), end-stage renal disease (Kurkijarvi R et al., Eur. J. Immunol., 2001, 31, 2876-2884), multiple sclerosis (Airas L et al., J. Neuroimmunol., 2006, 177, 132-135), inflammatory liver diseases (Kurkijarvi R et al., J. Immunol., 1998, 161, 1549-1557), psoriasis (Madej A et al., J. Eur. Acad. Dermatol. Venereol., 2007, 21, 72-78), Alzheimer's disease (del Mar Hernandez M et al., Neurosci. Lett., 2005, 384, 183-187; Ferrer I et al., Neurosci. Lett., 2002, 321, 21-24) and myopathies (Olive M et al., Muscle Nerve, 2004, 29, 261-266). A role for SSAO/VAP-1 in apoptosis, possibly leading to vascular tissue damage and atherogenesis has been implicated.

An oxime prodrug approach for ketone drugs, the non-steroidal antiinflammatory drugs ketoprofen and nabumetone, has been reported recently (Kumpulainen H, J. Med. Chem., 2006, 49, 1207-1211). The oxime structure was activated to the ketone with simultaneous release of nitric oxide (NO).

Because of its proposed involvement in a number of inflammatory processes and various pathologies, there is a great demand for inhibitors of SSAO/VAP-1 that can have therapeutic value in the prevention or the treatment of disorders or diseases associated with an elevated level or overexpression of SSAO/VAP-1, said diseases involving acute and chronic inflammations, diseases related to carbohydrate metabolism, diabetes-associated complications, diabetic retinopathy and macular oedema, diseases related to adipocyte or smooth muscle dysfunctions, neurodegenerative diseases and vascular diseases.

Several small-molecule inhibitors of SSAO/VAP-1 have been identified: hydrazine derivatives, phenylallylhydrazines (WO2006/094201, WO2005/014530), hydrazino alcohols and hydrazino indanes (WO2002/0202090, WO2003/006003, WO2005/080319), arylalkylamines, propenyl- and propargylamines, oxazolidinones, haloalkylamines, 1,3,4-oxadiazines (WO2002/0202541), 4,5,6,7-tetrahydroimidazo [4,5-c] pyridines (WO2002/0238153), thiocarbamoyl derivatives, carboxamides and sulfonamides (WO2006/013209, US2007/066646), thiazole derivatives (WO2004/087138, WO2004/067521, WO2006/028269, WO2006/011631), compounds disclosed in WO2005/082343; (compounds reviewed in: Matyus P et al., Curr. Med. Chem., 2004, 11, 1285-1298; Dunkel P et al., Curr. Med. Chem., 2008, 15, 1827-1839). Further relevant documents are mentioned in "Disclosure of the Invention" part below.

We now found that SSAO inhibitors, in particular a special class of compounds containing an oxime group and an unsaturated ring system joining to the carbon atom of the oxime group, optionally through an alkylene moiety, and 2-phenyl-2-propen-1-yl)hydrazine [2-phenylallylhydrazine; see e.g. in Tetrahedron Letters, 36, 3155-3158 (1977), WO2006/094201 and WO2005/014530] exhibit potent analgesic effects in traumatic neuropathy and neurogenic inflammation.

These pathophysiological conditions are mediated by the mechanical damage of peptidergic sensory nerves (in case of traumatic neuropathy) or chemical activation of peptidergic sensory nerves (in case of neurogenic inflammation), resulting in pathological activation and dysfunctions of peptidergic sensory nerves. The undesired activation and dysfunction is implicated in severe hyperalgesia (the threshold of a painful stimulus causing nocifensive behaviour remarkably decreases) and allodynia (non-painful stimulus becomes painful and induces nocifensive behaviour).

Traumatic neuropathy induced by mechanical nerve damage (e.g. suffered in accidents, bone fractures or operations) is mediated by complex mechanisms at the levels of both the peripheral and central nerve endings in the respective innervated region, spinal dorsal horn and other pain-related brain regions. These are completely different mechanisms than the ones involved in metabolic (diabetic) and toxic polyneuropathic conditions, therefore, the present invention may by no means be considered to be derived and extrapolated from the currently documented relations of SSAO and diabetic complications. Metabolic neuropathies (caused by diabetes, uremia etc.) and toxic neuropathies (caused by chemotherapeutic agents, alcohol etc.) are polyneuropathies affecting the nerves throughout the body. They are primarily due to severe biochemical abnormalities within the neurons. In case of diabetic neuropathy, these pathological changes are the consequences of hyperglycemia resulting in the damage of blood vessels around the nerve fibres and also detrimental changes in the metabolic state of the neurons (Kles K K and Vinik A I, Curr. Diab. Rev., 2006, 2, 131-145). These abnormalities lead to the production of free radicals and activation of some signal transduction pathways inducing neural dysfunctions (Ceriello A, Diabetes Care, 2003, 26, 1589-1596).

However, neuropathies caused by traumatic events (mechanical damage-induced axonopathies) affect only one or a few anatomical structures (mononeuropathy) and result in pathological activation and dysfunctions of peptidergic sensory nerves. In these cases, neuropathic pain is caused by different mechanisms compared to metabolic or toxic polyneuropathies, such as abnormal crosstalk between sensory and sympathetic nerves, changes in the expression of different ion channels, marked glial cell activation etc., and mediated by different signaling molecules than in diabetic neuropathy (Banoliel R et al., Oral Dis., 2012, 18(4):317-32; Aley K O. and Levine J D, Neuroscience., 2002, 111(2): 389-97). There are also differences in the therapy of diabetic and traumatic neuropathies. Causal pharmacotherapeutic agents (alpha-lipoic acid, benfotiamine) exerting an action based on the pathophysiological mechanism of the disease is only available in diabetic, but not in traumatic neuropathy (Miranda-Massari J R et al., Curr Clin Pharmacol., 2011, 6(4):260-73). Drugs used as symptomatic therapy for diabetic neuropathic pain include antidepressants, anticonvulsants, opioids and some other groups (e.g.: topical lidocain, capsaicin). Their effectiveness is well documented by clinical evidence-based data in painful polyneuropathies (such as diabetic) and postherpetic neuralgia, but not in traumatic neuropathy. Additionally, these drugs do not treat the cause of neuropathic pain and are not effective in a large proportion of patients (Finnerup et al., Pain., 2010, 150(3):573-81).

Peripheral and central sensitization mechanisms play important roles in the development of severe persistent chronic pain induced by mechanical nerve damage, which is not effectively treated by the conventional analgesics. Therefore, intensive traumatic neuropathic pain is a clinically challenging problem, since opioids and cyclo-oxygenase (COX) inhibitor non-steroidal anti-inflammatory agents (NSAIDs) are not potent in these conditions. Adjuvant analgesics, such as certain antiepileptics and antidepressants acting in the central nervous system (CNS) by inhibiting the ascending pain pathway and/or activating the descending inhibitory pathway can be used in some patients, but they cannot be regarded as optimal therapeutic solutions for the problems due to severe acute side effects (cardiovasular, CNS) and/or chronic toxicity.

Furthermore, neurogenic inflammation (vasodilatation, plasma protein extravasation, inflammatory cell activation) induced by the stimulation of peptidergic sensory nerves and the released pro-inflammatory sensory neuropeptides (substance P, calcitonin gene-related peptide) play a very important role in a variety of different acute and chronic inflammatory painful diseases (Chiu et al., Nat. Neurosci., 2013, 15(8):1063-7.), although it is not the exclusive mechanism. This is a basically different inflammatory mechanism compared to immune cell-mediated processes, it is often the very early initiation step even in chronic diseases, which triggers and then remarkably augments further cellular pathways. The neurogenic inflammatory component is not inhibited by the conventional anti-inflammatory drugs (COX inhibitors), and glucocorticoids are only moderately effective in extremely high doses in which they exert very many severe side-effects that limit their clinical applications. Therefore, it is particularly important to identify novel therapeutical mechanisms and targets to inhibit neurogenic inflammatory pain. This could substantially help the treatment of chronic inflammatory disorders providing long-term therapeutical benefits for a great patient population.

SUMMARY OF THE INVENTION

1. The invention relates to a compound having SSAO/VAP-1 inhibitor activity for use in the treatment of hyperalgesia and allodynia implicated in traumatic neuropathy or neurogenic inflammation.

With other wording: the invention relates to a compound having SSAO/VAP-1 inhibitor activity for use in the inhibition of pathological activation and dysfunctions of peptidergic sensory nerves caused by mechanical damage or chemical activation of peptidergic sensory nerves in neurogenic inflammation.

2. The compound mentioned in above point 1 in a preferred embodiment has the general formula of Ar—(CH2)n-CR1=N—OR2 (I') or salt, hydrate or solvate thereof—wherein Ar is a group of the formula:

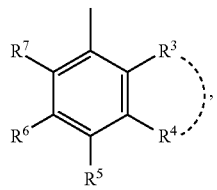
(a)

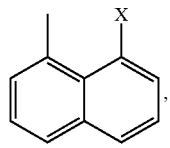
(b)

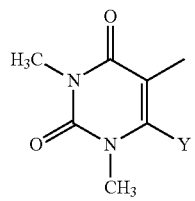
(c)

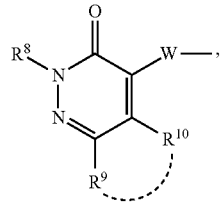
(d)

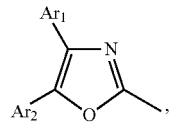
(e)

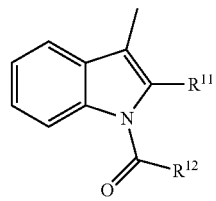
(f)

R1 is H or lower alkyl;
R2 is H, lower alkyl, benzyl, —(CH2)k-COOR13, —(CH2)m-N(R14R15) or —CO—NH—R16,
wherein R13 is lower alkyl,
k is 1, 2 or 3, preferably 1;
m is 1, 2 or 3; preferably 2;
R14 and R15 are independently from each other lower alkyl, or R14 and R15 together with the nitrogen they are attached form a 5 to 7 membered heteroring, optionally containing 1 to 3 further heteroatom(s) selected from nitrogen, oxygen and sulfur atoms,
R16 is phenyl, optionally substituted with one or more group selected from halogen, lower alkyl and lower alkoxy;
R3 and R4 together with the carbons they are attached to form a 5 to 7 membered heteroring containing one or two oxygen(s), preferably 1,3-dioxolane, optionally substituted with lower alkyl, preferably with methyl; or
R3 is H, halogen, lower alkyl or OR17, wherein R17 is H, lower alkyl, lower alkenyl, optionally substituted with phenyl;
R4 is H or OR19, wherein R19 is lower alkyl;
R5 is H or halogen;
R6 is H or halogen;
R7 is H, halogen, OH, OR20 or a phenyl substituted with Z
wherein R20 is lower alkyl or lower alkenyl, and Z is —CH=N—OH or halogen;
X is a 5 to 7 membered heteroring containing 1 or 3 heteroatom(s) selected from nitrogen, oxygen and sulfur atoms;
Y is SR21, OR22, 5 to 7 membered heteroring containing 1 to 3 heteroatom(s) selected from nitrogen, oxygen and sulfur atoms, optionally substituted with phenyl or a (lower alkenyl)amino, optionally N-substituted with lower alkyl;
wherein R21 is lower alkyl or phenyl and R22 is lower alkyl;
R8 is lower alkyl or optionally substituted benzyl, wherein the substituent is 1 or 2 lower alkoxy, preferably methoxy;
R9 is H or phenyl;
R10 is di(lower alkyl)amino, preferably dimethylamino, 5 to 7 membered heteroring containing 1 or 3 heteroatom(s) selected from nitrogen, oxygen and sulfur atoms, optionally substituted with one or more group selected from lower alkyl, lower alkenyl and phenyl;

or R9 and R10 together with the attached carbon atoms form an optionally substituted 5 to 8 membered heteroring containing 1 or 3 heteroatom(s) selected from nitrogen, oxygen and sulfur atoms, optionally substituted with one or more group selected from lower alkyl and benzyl, and optionally together with lower alkylene form a fused bicyclic group;

W is a bond or a phenylene group, preferably 1,2-phenylene group;

R11 is lower alkyl;

R12 is phenyl, optionally substituted with halogen; preferably with chloro;

n is integer of 0 to 4, preferably 0, 1 or 2;

Ar1 and Ar2 are the same or different and stand for phenyl, optionally substituted with one or more group selected from halogen, lower alkyl and lower alkoxy, preferably both are phenyl;

and any stereoisomer, mixture of stereoisomers, E or Z forms, mixture of E and Z forms, crystalline form, non-crystalline form thereof;

wherein

"lower alkyl" refers to aliphatic and alicyclic groups including straight-chain (linear), branched-chain or cyclic groups having up to 6 carbon atoms;

"lower alkenyl" refers to unsaturated aliphatic and alicyclic groups including straight-chain (linear), branched-chain, cyclic groups, and combinations thereof, having up to 6 carbon atoms, which contain at least one double bond (—C=C—);

"lower alkoxy" refers to a "(lower alkyl)-O—" group, where the "lower alkyl" has the above-defined meaning—for use in the prevention or treatment of a SSAO/VAP-1 related disease.

3. More preferably, the compound according to above point 2 is selected from the following group:
3-methoxy-2-methylbenzaldehyde oxime;
8-Pyrrolidino-1-naphthaldehyde oxime;
5-Hydroxy-1,3-benzodioxole-4-carbaldehyde oxime;
5-Ethoxy-1,3-benzodioxole-4-carbaldehyde oxime;
5-(Allyloxy)-1,3-benzodioxole-4-carbaldehyde oxime;
5-Bromo-1,3-benzodioxole-4-carbaldehyde oxime;
5-{2-[(Hydroxyimino)methyl]phenyl}-1,3-benzodioxole-4-carbaldehyde oxime;
6-Ethoxy-1,3-dimethyl-2,4-dioxo-1,2,3,4-tetrahydropyrimidine-5-carbaldehyde oxime;
6-Methoxy-1,3-dimethyl-2,4-dioxo-1,2,3,4-tetrahydropyrimidine-5-carbaldehyde oxime;
1,3-Dimethyl-2,4-dioxo-6-propoxy-1,2,3,4-tetrahydropyrimidine-5-carbaldehyde oxime;
6-Ethoxy-1,3-dimethyl-2,4-dioxo-1,2,3,4-tetrahydropyrimidine-5-carbaldehyde-O-methyloxime;
1,3-Dimethyl-2,4-dioxo-6-(propylthio)-1,2,3,4-tetrahydropyrimidine-5-carbaldehyde oxime;
1,3-Dimethyl-6-(methylthio)-2,4-dioxo-1,2,3,4-tetrahydropyrimidine-5-carbaldehyde oxime;
6-(Ethylthio)-1,3-dimethyl-2,4-dioxo-1,2,3,4-tetrahydropyrimidine-5-carbaldehyde oxime;
1,3-Dimethyl-2,4-dioxo-6-(phenylthio)-1,2,3,4-tetrahydropyrimidine-5-carbaldehyde oxime;
6-(Ethylthio)-1,3-dimethyl-2,4-dioxo-1,2,3,4-tetrahydropyrimidine-5-carbaldehyde-O-methyloxime;
6-[Allyl(methyl)amino]-1,3-dimethyl-2,4-dioxo-1,2,3,4-tetrahydropyrimidine-5-carbaldehyde oxime;
3-(4,5-Diphenyl-1,3-oxazol-2-yl)propanal oxime and
1-(4-Chlorobenzoyl)-2-methyl-1H-indole-3-carbaldehyde oxime, or any stereoisomer, mixture of stereoisomers, E or Z forms, mixture of E and Z forms, crystalline form, non-crystalline form, hydrate, solvate or salt thereof.

4. In a more preferred embodiment the compound according to above point 3 is the 3-(4,5-diphenyl-1,3-oxazol-2-yl)propanal oxime (see also as SZV-1287 in the following parts).

5. The compound mentioned in above point 1 in a preferred embodiment is the (2-phenyl-2-propen-1-yl)hydrazine (see also as SZV-1911 in the following parts) or pharmaceutically acceptable salt thereof. The pharmaceutically acceptable salts of this compound are acid addition salts, e.g. hydrochloride, hydrobromide, fumarate.

The compounds given in the above points 3 to 5 are those type SSAO/VAP-1 inhibitor compounds which contain an oxime group and an unsaturated ring system joining to the carbon atom of the oxime group, optionally through an alkylene moiety. Some further details of the above definitions and the preparation of the above compounds are discussed in details in WO 2010/029379 A1.

DETAILED DESCRIPTION OF THE INVENTION

As a result of intensive studies, the present inventors have made the unexpected observation that SSAO/VAP-1 inhibition effectively inhibits neuropathic mechanical hyperalgesia both in rat and mouse models of (I) traumatic nerve injury, as well as (II) neurogenic inflammatory hyperalgesia.

The operation-induced decrease of the touch sensitivity threshold is considered to be allodynia in the rat, since the mechanical stimulus is basically not painful, but hyperalgesia in the mouse, because its paw is much smaller and the force applied on the plantar surface is a mild painful stimulus also in intact animals. We showed for the first time that two SSAO/VAP-1 inhibitors, SZV-1911 and SZV-1287, significantly decreased sciatic nerve ligation-induced neuropathic mechanical allodynia and hyperalgesia, as well neurogenic inflammatory hyperalgesia developing in response to central sensitization mechanisms. Meanwhile although they did not influence neuropathic cold hyperalgesia, they moderately decreased acute neurogenic inflammatory heat allodynia (it was only significant in case of SZV-1287 after RTX) mediated by peripheral sensitization processes. These surprising findings indicate a predominantly central analgesic action of these compounds, which is absolutely novel.

The partial sciatic nerve ligation-induced nerve damage model is a well-established and widely used traumatic mononeuropathy model with a complex mechanism (Tanabe et al., J Neurosci Res., 2008, 86(15):3258-64), which is completely different from diabetic neuropathy or inflammatory pain. Although peripheral sensitization at the level of the nerve terminals in the hindlimbs are involved as shown by the cold tolerance decrease (cold allodynia), central sensitization is very important in the developing mechanical hyperalgesia described by the mechanonociceptive threshold (the lowest mechanical stimulus evoking nocifensive behaviour) decrease (Campbell and Meyer, Neuron., 2006, 52(1):77-92; Foulkes and Wood, Channels (Austin). 2007, 1(3):154-60.).

RTX- and formalin activate TRPV1 and TRPA1 ion channels on sensory nerves and induce pro-inflammatory neuropeptide release resulting in nerve terminal sensitization at the periphery and later also centrally. This neurogenic inflammatory pain component contributes significantly to the initiation of a complex neuro-immune interaction in several chronic inflammatory processes, triggers and aggravates the severity. In the formalin test animals exhibit acute nocifensive reaction as a behavioural result of a complex reflex: the early phase (0-5 min) reflects direct sensory nerve activation (acute somatic chemonociception), which is not inhibited by conventional analgesics, and the later phase (20-45 min) is related to the nerve terminal sensitization after the sensory neuropeptide release and acute neurogenic inflammation. Beside these characteristic nocifensive behaviours, there is an early thermal allodynia due to peripheral and later developing mechanical hyperalgesia in response to central sensitization, respectively. All these informative and disease-related parameters can be simultaneously and reliably investigated in this well-established mechanism model (McNamara et al., Proc Natl. Acad. Sci. USA, 2007, 104(33):13525-30.).

SUMMARY OF DRAWINGS

FIGS. 1 A and B: The test protocol is shown schematically for measurement of the mechanical touch sensitivity and cold tolerance in the traumatic mononeuropathy model in rats (A) and mice (B).

FIGS. 2 A and B: Effect of SZV-1911 and SZV-1287 on sciatic nerve ligation-induced mechanical allodynia on the injured (A) and the controlateral (B) paw of the rats 7 days after the operation in comparison with the vehicle.

FIGS. 3 A and B: Effect of SZV-1911 and SZV-1287 on the mechanonociceptive thresholds of the ipsilateral (A) and of the contralateral (B) paw of sham-operated rats in comparison with the vehicle.

FIGS. 4 A-D: Effect of SZV-1911 (A-B) and SZV-1287 (C-D) on the mechanonociceptive thresholds of the injured paw of sciatic nerve operated mice in comparison with the vehicle on Day 3 and on Day 7, respectively.

FIGS. 5 A-D: Effect of SZV-1911 (A-B) and SZV-1287 (C-D) on the paw withdrawal latency of the injured paw of sciatic nerve operated mice in comparison with the vehicle on Day 3 and on Day 7, respectively.

FIGS. 6 A and B: The test protocol is shown schematically for measurement of the noxious heat thresholds and mechanonociceptive thresholds after i. pl. resiniferatoxin (A) and formalin (B) administration.

FIGS. 7 A and B: Effects of SZV-1911 and SZV-1287 on RTX-induced thermal (A.) and mechanical (B.) hyperalgesia in mice in comparison with the vehicle.

FIGS. 8 A-C: Effects of SZV-1287 on formalin-induced acute nocifensive reactions (A) and the drop of thermo-(B) and mechanonociceptive (C) thresholds of mice.

METHODOLOGY

Experimental Models, Protocols and Measuring Techniques

Solution Preparation

The solutions were prepared freshly on the day of the experiment with sterile saline. SZV-1287 (prepared according to WO 2010/029379 A1) dissolved in saline and the solution was clear. The SZV-1911 (prepared according to WO2006/094201 and WO2005/014530) solution was prepared with Tween 80 and ethanol, stirred properly with a vortex, heated moderately to 42° C. and sonicated, but it was still opalescent. The i.p. administered volume was 0.2 ml/100 g body weight from 10 mg/ml in rats solution and 0.1 m/10 g body weight from 2 mg/ml solution to achieve the 20 mg/kg doses. The solvent of SZV-1911 was given to the vehicle-treated animals in the same volume.

Experimental Animals and Ethical Issues

Sciatic nerve ligation-induced traumatic mononeuropathy experiments were performed on male Wistar rats (250-300 g), and on male C57Bl/6 mice as well as resiniferatoxin- or formalin-induced hyperalgesia. The original breeding pairs of the animals were purchased from Charles River Ltd. All the animals were kept in the Animal Facility of the Department of Pharmacology and Pharmacotherapy at the University of Pécs at 24-25° C. provided with standard chow and water ad libitum.

All experimental procedures were carried out according to the European Communities Council Directive of 86/609/EEC. The studies were approved by the Ethics Committee on Animal Research, University of Pecs. All efforts were made to minimize animal-suffering, to reduce number of used animals and to utilize in vivo techniques if available.

I. Neuropathy Models

Experimental Protocol, Model and Investigational Techniques

Before all experiments one conditioning and three reliable control threshold measurements were performed on three consecutive days. All operations were performed by the same operator, who was blinded to the animal group assignments and the treatment allocation (FIG. 1A for the rat, B for the mouse experimental paradigm).

Investigation of Mechanical Hyperalgesia and Cold Allodynia in Sciatic Nerve Ligation-Induced Traumatic Mononeuropathy On the $3^{rd}$ and on the $7^{th}$ day following the nerve ligation, the mechano-nociceptive thresholds were determined directly before and 15 min after i.p. drug administration to observe the difference between pre-injection and post-injection thresholds in mice. We determined the developing cold allodynia following the sciatic nerve ligation at Days 3 and 7. In rats we examined the developing mechanical allodynia just 7 days after the sciatic nerve ligation on the same way like in mice. Only animals with a minimum of 25% hyperalgesia/allodynia were included in the study (Seltzer et al., Pain., 1990, 43(2):205-18; Pintér et al., Naunyn Schmiedebergs Arch Pharmacol., 2002, 366(2):142-50.).

The Sciatic Nerve Operation Procedure

Mice were anaesthesized with a combination of ketamine and xylazine (100 mg/kg and 5 mg/kg i.p. respectively), but in rats Na-pentobarbital (40 mg/kg i.p) were used. The common sciatic nerve was exposed unilaterally on the right side high in the thigh and ⅓-½ of the nerve trunk was carefully separated and tightly ligated using a siliconised silk suture (Ethicone 5-0 and 8.0, respectively). Then the wound was closed and the animals were allowed to survive for 8 days (Seltzer, 1990; Malmberg and Basbaum 1998; Bolcskei et al. 2005; Sandor et al. 2010). During this period, signs of spontaneous pain (holding the legs in elevated position transiently for 2-3 days) and mechanical hyperalgesia and cold allodynia developed. In order to investigated the efficacy of these drugs we examined the drop of the mechanical touch sensitivity on Day 3, however the decrease of the mechanical threshold develops fully 7 days after the surgery.

Cold Stimulation

A noxious cold stimulus was applied by immersing one of the murine hindpaws in icy water, remaining the temperature steady at 0° C. Cold perception was assessed as the time taken by the animal to pulling out its paw from the cold water, the cut-off time was 180 seconds. The paw withdrawal behaviour represents a consistent and reproducible method for the determination of the hypersensitivity of cold nociception after sciatic nerve ligation.

Measurement of the Mechanical Touch Sensitivity

The mechanical touch sensitivity thresholds of the plantar surface of the paws was determined by aesthesiometry (Ugo Basile Dynamic Plantar Aesthesiometer 37400; Comerio, Italy). This is an electronic von Frey device, in which the animals moved about freely in one of the compartments of the enclosure positioned on the metal mesh surface. Following acclimation after cessation of exploratory behaviour, the touch stimulator unit was placed under the animal's paw, using the adjustable angled-mirror to position the filament below the target area of the plantar surface. Then an electrodynamic actuator of proprietary design lifted a straight metal filament, which touched the plantar surface and began to exert an increasing upward force at a preset rate of application until a stop signal (removal of the paw) was attained. The paw withdrawal threshold was obtained in grams. Hyperalgesia or allodynia (decrease of the withdrawal thresholds) was expressed as percentage by comparing the data of each individual animal to the averaged three initial control thresholds.

Statistical Analysis

Results are expressed as the mean±s.e.m. The pre-drug and the post-drug data pairs within each group were compared with 2-way ANOVA following Bonferroni's post-test. *$p<0.05$, $p<0.01$; *$p<0.001$ were considered to be significant.

The test protocol is shown schematically on FIGS. 1 A and B.

Analgesic Action of SSAO Inhibitors in Traumatic Mononeuropathy

Effects on Sciatic Nerve Ligation-Induced Hyperalgesia in Rats

Seven days after the nerve ligation an approximately 40-50% mechanical allodynia developed on the operated limb of the rats. The vehicle (0.2 ml/100 g body weight) did not alter the mechanical allodynia 15 minutes later (41.5+7.2% vs 46.7+5.7% pre-injection value), but pretreatment with the 20 mg/kg i.p. doses of both SZV-1287 and SZV-1911 significantly reduced the 48.8±6.2% and 47.8±7.9% pre-injection allodynia to 34.6±7.6% and 32.9±3.4%, respectively. The approximately 30% inhibitory effects of the two compounds did not differ significantly from each other. No change of the mechanonociceptive thresholds was detected either on the contralateral side of the operated (FIG. 2.B) or in the sham-operated group. The results are shown in FIGS. 2 A and B.

Allodynia values were calculated as % by comparing the mechano-nociceptive thresholds measured on the 7$^{th}$ day to the mean initial threshold values. Column pairs represent allodynia before drug injection and 15 min after compound/vehicle administration. Results are expressed as means±s.e.m. of the mechanonociceptive threshold changes of n=7 rats in the vehicle-treated and 8-8 rats in both compound-treated groups. Data were analysed with One-way ANOVA following Bonferroni's post-test in comparison to determine differences between the pre- and post-injection values of the respective groups, *$p<0.05$.

The effects of SZV-1911 and SZV-1287 on the mechanonociceptive thresholds of the ipsilateral (A) and of the contralateral (B) paw of sham-operated rats in comparison with the vehicle are shown on FIGS. 3A and 3B.

Effects on Sciatic Nerve Ligation-Induced Hyperalgesia in Mice

Investigating the effects of SSAO inhibitors we performed the sciatic nerve ligation in TRPA1 wildtype mice. 3 days after the operation the developing mechanical hyperalgesia was approximately 40% in all groups which was even increased on Day 7. The hyperalgesia was significantly diminished to 15 minutes after the i.p. administration of a single dose of 20 mg/kg SZV-1911 compared to their postoperative control values.

Investigating the cold allodynia which is a symptom of the sciatic nerve ligation caused traumatic mononeuropathy, we did not observed any significant changes.

The effects of SZV-1911 (A-B) and SZV-1287 (C-D) on the mechanonociceptive thresholds of the injured paw of sciatic nerve operated mice in comparison with the vehicle on Day 3 and on Day 7, respectively, are shown on FIGS. 4 A, B, C and D.

The mechanical hyperalgesia values were determined as % by comparing the nociceptive thresholds measured on day 3 and 7 after the operation to the mean initial mechanonociceptive threshold values. Column pairs represent hyperalgesia before drug injection and 15 min after compound/solvent administration. Results are expressed as means±s.e.m. of the thermo- and mechanonociceptive threshold changes of n=6-6 in the vehicle/compound-treated TRPA1$^{+/+}$ as well as TRPA1$^{-/-}$ mice groups. Data were analysed with One-way ANOVA following Bonferroni's post-test in comparison to determine differences between the pre- and post-injection values of the respective groups. *$p<005$ The effects of SZV-1911 (A-B) and SZV-1287 (C-D) on the paw withdrawal latency of the injured paw of sciatic nerve operated mice in comparison with the vehicle on Day 3 and on Day 7, respectively, are shown on FIGS. 5 A, B, C and D.

The paw withdrawal latency values were determined as % by comparing the latencies measured on day 3 and 7 after the operation to the mean initial latency values. Column pairs represent the change of paw withdrawal latency before drug injection and 15 min after compound/solvent administration. Results are expressed as means±s.e.m of the withdrawal behaviour latency changes of n=6-6 mice per groups. Data were analysed with One-way ANOVA following Bonferroni's post-test in comparison to determine differences between the pre- and post-injection values of the respective groups.*$p<0.05$.

II. Neurogenic Inflammation Models

Resiniferatoxin-Evoked Thermal and Mechanical Hyperalgesia

Resiniferatoxin (RTX) is a potent agonist of Transient Receptor Potential Vanilloid 1 (TRPV1) receptors, which are mainly expressed on capsicin-sensitive sensory nerve ending. Intraplantarly (i.pl.) injection of RTX (0.03 μg/ml; 20 μl) into one of the hindpaws induced an acute inflammation and a robust drop of heat and mechanical thresholds. After applying single dose of pretreatment –10 minutes before testing-, thermonociceptive measuring were repeated at 5, 10, 15, 20 minutes, while mechanonociceptive testing was observed at 2, 4, 6, 24 hours.

Formalin—Induced Acute Somatic Nocifensive Behaviour

Formalin (Formaldehydum solutum 37%; Ph.Hg. VII.; 20 μl, 2.5%, i.pl.) injected into the right hindpaw known as a selective agonist of Transient Receptor Potential Ankyrin 1 (TRPA1) induces nocifensive reactions in two phases, the firea of which (0-5 min) is thought to be due to a direct chemonociceptive effect of formalin, while the second one (20-45 min) is mainly mediated by inflammatory reactions (Tjolsen et al., 1992). After applying single dose of pretreatment -10 minutes before testing-, thermonociceptive measuring was performed at 1 hour while mechanonociceptive testing was observed at 2, 4 hours.

Determination of the Noxious Heat Thresholds

The noxious heat threshold of the paw, defined as the lowest temperature evoking nocifensive behaviour—was measured with an increasing-temperature hot plate (IITC Life Science, Woodland Hills, Calif., USA). After habituation, mice were placed onto the plate, which was then heated up from room temperature at a rate of 12° C./min until the animals showing nocifensive behaviour (licking, lifting or shaking one of the hindpaws). The corresponding plate temperature was considered as the noxious heat threshold.

The test protocol is shown schematically on FIGS. 6 A and B.

Effects on RTX-Induced Hyperalgesia

The average control heat threshold value was 43.73±0.5° C. in male C57Bl/6 animals. The intraplantarly administration of RTX caused firstly, after few minutes a robust drop of heat threshold, approx. 8 degree in solvent pretreated animal group. This decrease was significantly lower (1-2° C.) in mice injected intraperitoneally pretreatment with 20 mg/kg SZV-1287, and maintained during 15 minutes. Two hours after the application the mechanical hyperalgesia was developed. The change of the mechanonociceptive threshold in solvent treated group was 47.1±6% at 2 hours and 35.3±3% at 4 hours. These changes were significantly reduced in SZV-1911 injected group, 14.7±6% and 6.5±6% respectively at 2 and 4 hours. This drop of mechanonociceptive threshold was 22.1±7% in SZV-1287 treated group at 2 hours.

The effects of SZV-1911 and SZV-1287 on RTX-induced thermal (A) and mechanical (B) hyperalgesia in mice in comparison with the vehicle are shown on FIGS. 7 A and B.

Lines represent thermal and mechanical hyperalgesia before drug injection and 5, 10, 15, 20 min as well as 2, 4, 6, 24 hours, respectively after compound/solvent administration. Results are expressed as means±s.e.m. of the thermo- and mechanonociceptive threshold changes of n=7-8 per groups. Data were analysed with Two-way ANOVA following Bonferroni's post-test in comparison to determine differences between the pre- and post-injection values of the respective groups p<0.01, * p<0.001 SZV-1287 vs. saline and ### p<0.001 SZV-1911 vs. saline.

Effects on Formalin-Induced Acute Nocifensive Behaviours and Hyperalgesia

Nocifensive behaviour expressed as the total duration of paw lickings and liftings was significantly lower in mice treated with SZV-1287 both in the early phase (0-5 min) referring to acute chemonociception and late phase (20-45 min) evoked by the inflammatory reaction.

The basal thermonociceptive thresholds were 44.8±1.7 and 44.9±0.7° C. which were significantly reduced by formalin application to 37.5±4 and 37.4±3° C. in SZV-1287 treated as well as in saline treated mice, respectively.

The effects of SZV-1287 on formaline-induced acute nocifensive reactions (A) and the drop of thermo-(B) and mechanonociceptive (C) thresholds of mice are shown on FIGS. 8 A, B and C.

The total duration of paw licking and lifting were expressed to representing the nociceptive behaviour. Column pairs represent thermal hyperalgesia before drug injection and 1 hour after compound/solvent administration. Mechanical hyperalgesia values were determined as % by comparing the nociceptive thresholds measured at 2 and 4 hours after the application to the initial threshold values.

Results are expressed as means±s.e.m. of the thermo- and mechanonociceptive threshold changes of n=11-11 animals/groups. Data were analysed with One-way ANOVA following Bonferroni's post-test in comparison to determine differences between the pre- and post-injection values of the respective groups.

The invention claimed is:

1. A method for the treatment of hyperalgesia and allodynia implicated in traumatic neuropathy or neurogenic inflammation, said method comprising administering a compound having SSAO/VAP-1 inhibitor activity to a subject in need of said treatment, wherein the compound has the general formula of Ar—(CH2)n-CR1=N—OR2 (I') or salt, hydrate or solvate thereof—wherein Ar is a group of the formula:

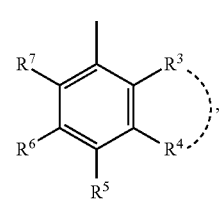

(a)

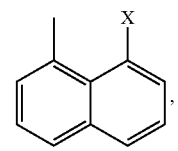

(b)

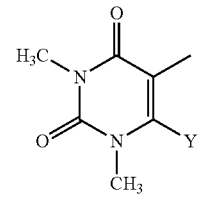

(c)

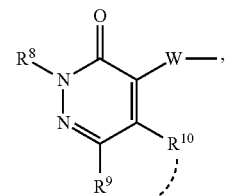

(d)

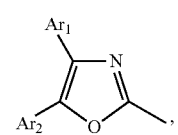

(e)

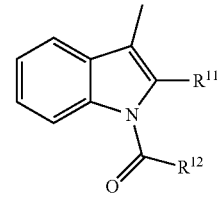

(f)

R1 is H or lower alkyl;
R2 is H, lower alkyl, benzyl, —(CH2)k-COOR13, —(CH2)m-N(R14R15) or —CO—NH—R16, wherein R13 is lower alkyl,
k is 1, 2 or 3;
m is 1, 2 or 3;
R14 and R15 are independently from each other lower alkyl, or R14 and R15 together with the nitrogen they are attached form a 5 to 7 membered heterering, optionally containing 1 to 3 further heteroatom(s) selected from nitrogen, oxygen and sulfur atoms,
R16 is phenyl, optionally substituted with one or more group selected from halogen, lower alkyl and lower alkoxy;
R3 and R4 together with the carbons they are attached to form a 5 to 7 membered heterering containing one or two oxygen(s), preferably 1,3-dioxolane, optionally substituted with lower alkyl; or
R3 is H, halogen, lower alkyl or OR17, wherein R17 is H, lower alkyl, lower alkenyl, optionally substituted with phenyl;
R4 is H or OR19, wherein R19 is lower alkyl;
R5 is H or halogen;
R6 is H or halogen;
R7 is H, halogen, OH, OR20 or a phenyl substituted with Z
wherein R20 is lower alkyl or lower alkenyl, and Z is —CH═N—OH or halogen;
X is a 5 to 7 membered heterering containing 1 or 3 heteroatom(s) selected from nitrogen, oxygen and sulfur atoms;
Y is SR21, OR22, 5 to 7 membered heterering containing 1 to 3 heteroatom(s) selected from nitrogen, oxygen and sulfur atoms, optionally substituted with phenyl or a (lower alkenyl)amino, optionally N-substituted with lower alkyl; wherein R21 is lower alkyl or phenyl and R22 is lower alkyl;
R8 is lower alkyl or optionally substituted benzyl, wherein the substituent is 1 or 2 lower alkoxy;
R9 is H or phenyl;
R10 is di(lower alkyl)amino, preferably dimethylamino, 5 to 7 membered heterering containing 1 or 3 heteroatom(s) selected from nitrogen, oxygen and sulfur atoms, optionally substituted with one or more group selected from lower alkyl, lower alkenyl and phenyl;
or R9 and R10 together with the attached carbon atoms form an optionally substituted 5 to 8 membered heterering containing 1 or 3 heteroatom(s) selected from nitrogen, oxygen and sulfur atoms, optionally substituted with one or more group selected from lower alkyl and benzyl, and optionally together with lower alkylene form a fused bicyclic group;
W is a bond or a phenylene group;
R11 is lower alkyl;
R12 is phenyl, optionally substituted with halogen;
n is integer of 0 to 4;
Ar1 and Ar2 are the same or different and stand for phenyl, optionally substituted with one or more group selected from halogen, lower alkyl and lower alkoxy;
and any stereoisomer, mixture of stereoisomers, E or Z forms, mixture of E and Z forms, crystalline form, non-crystalline form thereof;
wherein
"lower alkyl" refers to aliphatic and alicyclic groups including straight-chain (linear), branched-chain or cyclic groups having up to 6 carbon atoms;

"lower alkenyl" refers to unsaturated aliphatic and alicyclic groups including straight-chain (linear), branched-chain, cyclic groups, and combinations thereof, having up to 6 carbon atoms, which contain at least one double bond (—C═C—);
"lower alkoxy" refers to a "(lower alkyl)-O—"group, where the "lower alkyl"has the above-defined meaning.

2. The method of claim 1, wherein the compound is selected from the group consisting of:
3-methoxy-2-methylbenzaldehyde oxime;
8-Pyrrolidino-1-naphthaldehyde oxime;
5-Hydroxy-1,3-benzodioxole-4-carbaldehyde oxime;
5-Ethoxy-1,3-benzodioxole-4-carbaldehyde oxime;
5-(Allyloxy)-1,3-benzodioxole-4-carbaldehyde oxime;
5-Bromo-1,3-benzodioxole-4-carbaldehyde oxime;
5-{2-[(Hydroxyimino)methyl]phenyl}-1,3-benzodioxole-4-carbaldehyde oxime;
6-Ethoxy-1,3-dimethyl-2,4-dioxo-1,2,3,4-tetrahydropyrimidine-5-carbaldehyde oxime;
6-Methoxy-1,3-dimethyl-2,4-dioxo-1,2,3,4-tetrahydropyrimidine-5-carbaldehyde oxime;
1,3-Dimethyl-2,4-dioxo-6-propoxy-1,2,3,4-tetrahydropyrimidine-5-carbaldehyde oxime;
6-Ethoxy-1,3-dimethyl-2,4-dioxo-1,2,3,4-tetrahydropyrimidine-5-carbaldehyde-O-methyloxime;
1,3-Dimethyl-2,4-dioxo-6-(propylthio)-1,2,3,4-tetrahydropyrimidine-5-carbaldehyde oxime;
1,3-Dimethyl-6-(methylthio)-2,4-dioxo-1,2,3,4-tetrahydropyrimidine-5-carbaldehyde oxime;
6-(Ethylthio)-1,3-dimethyl-2,4-dioxo-1,2,3,4-tetrahydropyrimidine-5-carbaldehyde oxime;
1,3-Dimethyl-2,4-dioxo-6-(phenylthio)-1,2,3,4-tetrahydropyrimidine-5-carbaldehyde oxime;
6-(Ethylthio)-1,3-dimethyl-2,4-dioxo-1,2,3,4-tetrahydropyrimidine-5-carbaldehyde-O-methyloxime;
6-[Allyl(methyl)amino]-1,3-dimethyl-2,4-dioxo-1,2,3,4-tetrahydropyrimidine-5-carbaldehyde oxime;
3-(4,5-Diphenyl-1,3-oxazol-2-yl)propanal oxime and
1-(4-Chlorobenzoyl)-2-methyl-1H-indole-3-carbaldehyde oxime,
or any stereoisomer, mixture of stereoisomers, E or Z forms, mixture of E and Z forms, crystalline form, non-crystalline form, hydrate, solvate or salt thereof.

3. The method of claim 2, wherein the compound is the 3-(4,5-diphenyl-1,3-oxazol-2-yl)propanal oxime.

4. A method for the treatment of hyperalgesia and allodynia implicated in traumatic neuropathy or neurogenic inflammation, said method comprising administering a compound having SSAO/VAP-1 inhibitor activity to a subject in need of said treatment, wherein the compound is; (2-phenyl-2-propen-1-yl)hydrazine or pharmaceutically acceptable salt thereof.

5. The method of claim 1, wherein the subject is suffering from traumatic neuropathy or neurogenic inflammation.

6. The method of claim 1, wherein the subject is suffering from pathological activation and a dysfunction of peptidergic sensory nerves caused by mechanical damage or chemical activation.

7. The method of claim 1, wherein the subject is suffering from severe hyperalgesia or allodynia.

* * * * *